United States Patent
Schmid et al.

(10) Patent No.: US 10,959,882 B2
(45) Date of Patent: Mar. 30, 2021

(54) REFRACTIVE TREATMENT OF AN EYE BY PRINTING MATERIAL ONTO A TARGET

(71) Applicant: Novartis AG, Basel (CH)

(72) Inventors: Stefan Schmid, Neuendettelsau (DE); Berndt Warm, Schwaig (DE)

(73) Assignee: Alcon Inc.

( * ) Notice: Subject to any disclaimer, the term of this patent is extended or adjusted under 35 U.S.C. 154(b) by 82 days.

(21) Appl. No.: 16/251,949

(22) Filed: Jan. 18, 2019

(65) Prior Publication Data

US 2019/0240070 A1    Aug. 8, 2019

Related U.S. Application Data

(60) Provisional application No. 62/626,579, filed on Feb. 5, 2018.

(51) Int. Cl.
*A61F 9/008* (2006.01)
*A61F 9/007* (2006.01)
(Continued)

(52) U.S. Cl.
CPC .......... *A61F 9/00804* (2013.01); *A61F 2/147* (2013.01); *A61F 9/0081* (2013.01);
(Continued)

(58) Field of Classification Search
CPC .............. A61F 9/00804; A61F 9/00834; A61F 9/00836; A61F 2/145
See application file for complete search history.

(56) References Cited

U.S. PATENT DOCUMENTS

| 2013/0211387 A1* | 8/2013 | Riedel ................. A61F 9/008 606/4 |
| 2014/0264980 A1 | 9/2014 | Muller |

(Continued)

FOREIGN PATENT DOCUMENTS

| WO | 2015103524 A1 | 7/2015 |
| WO | 2016145021 A1 | 9/2016 |
| WO | 2017024090 A1 | 2/2017 |

OTHER PUBLICATIONS

Humeyra Karacal, et al.; "Intrastromal Corneal Ring Segments (ICRS)"; EyeWiki, American Academy of Ophthalmology; Jan. 20, 2015; pp. 1-6; obtained online from: http://eyewiki.aao.org/w/index.php?title=Intrastromal_Corneal_Ring_Segments_(ICR . . . .
(Continued)

*Primary Examiner* — Allen Porter
*Assistant Examiner* — Adreanne A. Arnold

(57) ABSTRACT

In certain embodiments, a system for performing refractive treatment of an eye comprises a laser, a printer, and a computer. The laser emits a laser beam to prepare the eye for the refractive treatment. The printer prints material onto a print area of a target. The printer comprises a printer head and a printer controller. The printer head directs the material onto the print area, and the printer controller moves the printer head to direct the material onto a specific location of the print area. The computer comprises a memory and processors. The memory stores instructions for a pattern for the target. The pattern is designed to provide the refractive treatment for the eye. The processors instruct the printer controller to move the printer head to print the material onto the print area according to the pattern.

19 Claims, 3 Drawing Sheets

(51) Int. Cl.
    *A61F 2/14*      (2006.01)
    *A61F 9/013*     (2006.01)
(52) U.S. Cl.
    CPC ...... *A61F 9/00812* (2013.01); *A61F 9/00834* (2013.01); *A61F 9/00836* (2013.01); *A61F 2/142* (2013.01); *A61F 2/1451* (2015.04); *A61F 9/00709* (2013.01); *A61F 9/013* (2013.01); *A61F 2009/00846* (2013.01); *A61F 2009/00851* (2013.01); *A61F 2009/00872* (2013.01); *A61F 2009/00893* (2013.01); *A61F 2009/00895* (2013.01); *A61F 2009/00897* (2013.01); *B32B 2307/412* (2013.01); *B32B 2307/418* (2013.01)

(56) References Cited

U.S. PATENT DOCUMENTS

| | | | | |
|---|---|---|---|---|
| 2016/0325499 | A1* | 11/2016 | Muller | B29C 64/20 |
| 2017/0027754 | A1* | 2/2017 | Muller | B23K 26/402 |
| 2019/0038373 | A1* | 2/2019 | Jung | A61F 9/00827 |
| 2019/0314145 | A1 | 10/2019 | Schmid | |
| 2020/0069466 | A1 | 3/2020 | Bornemann | |

OTHER PUBLICATIONS

Stacy L. Littlechild, et al.; "Fibrinogen, Riboflavin, and UVA to Immobilize a Corneal Flap—Molecular Mechanisms"; Investigative Ophthalmology & Visual Science; Sep. 2012; vol. 53; No. 10; pp. 5991-6003; obtained online from: iovs.arvojournals.org.

Wikipedia—Tissue Engineering; pp. 1-20; obtained online from https://en.wikipedia.org/wiki/Tissue_engineering.

Andreas Zynga; "Bio-materials—these substances are revolutionising construction, 3D-printing and more"; Biomaterials; Aug. 7, 2015; obtained online (website address: https://www.wiwo.de/technologie/green/biomaterialien-diese-stoffe-revolutionieren-bau-3d-druck-und-mehr/13552438.html).

Mark & Technik; "Micro-objective lenses on Cmos chips"; 3D Printer for Microfabrication; Mar. 24, 2017; obtained online (website address: https://www.elektroniknet.de/markt-technikielektronikfertigung/mikro-objektivlinsen-auf-cmos-chips-140042.html).

* cited by examiner

REFRACTIVE TREATMENT OF AN EYE BY PRINTING MATERIAL ONTO A TARGET

TECHNICAL FIELD

The present disclosure relates generally to refractive treatment of an eye, and more specifically to refractive treatment of an eye by printing material onto a target.

BACKGROUND

Refractive treatment of an eye refers to surgery performed to change the refractive properties of the eye to reduce refractive error in order to improve vision. Refractive error occurs when the shape of the eye does not bend light correctly, resulting in a blurred image. The main types of refractive errors are myopia (nearsightedness), hyperopia (farsightedness), presbyopia (loss of near vision with age), and astigmatism. Typical refractive treatments include laser in-situ keratomileusis (LASIK), photorefractive keratectomy (PRK), radial keratotomy (RK), astigmatic keratotomy (AK), automated lamellar keratoplasty (ALK), laser thermal keratoplasty (LTK), conductive keratoplasty (CK), and intracorneal ring (Intacs).

BRIEF SUMMARY

In certain embodiments, a system for performing refractive treatment of an eye comprises a laser, a printer, and a computer. The laser emits a laser beam to prepare the eye for the refractive treatment. The printer prints material onto a print area of a target. The printer comprises a printer head and a printer controller. The printer head directs the material onto the print area, and the printer controller moves the printer head to direct the material onto a specific location of the print area. The computer comprises a memory and processors. The memory stores instructions for a pattern for the target. The pattern is designed to provide the refractive treatment for the eye. The processors instruct the printer controller to move the printer head to print the material onto the print area according to the pattern.

In certain embodiments, a method for performing refractive treatment of an eye comprises emitting, from a laser, a laser beam to prepare the eye for the refractive treatment. A computer communicates with a printer configured to print material onto a print area of a target, where the printer comprises a printer head that directs the material onto the print area and a printer controller that moves the printer head to direct the material onto a specific location of the print area. The computer accesses instructions for a pattern for the target, where the pattern is designed to provide the refractive treatment for the eye. The computer instructs the printer controller to move the printer head to print material onto the print area according to the pattern.

BRIEF DESCRIPTION OF THE DRAWINGS

Embodiments of the present disclosure are described by way of example in greater detail with reference to the attached figures, in which.

DESCRIPTION OF EXAMPLE EMBODIMENTS

Referring now to the description and drawings, example embodiments of the disclosed apparatuses, systems, and methods are shown in detail. As apparent to a person of ordinary skill in the field, the disclosed embodiments are exemplary and not exhaustive of all possible embodiments.

Figure 1:
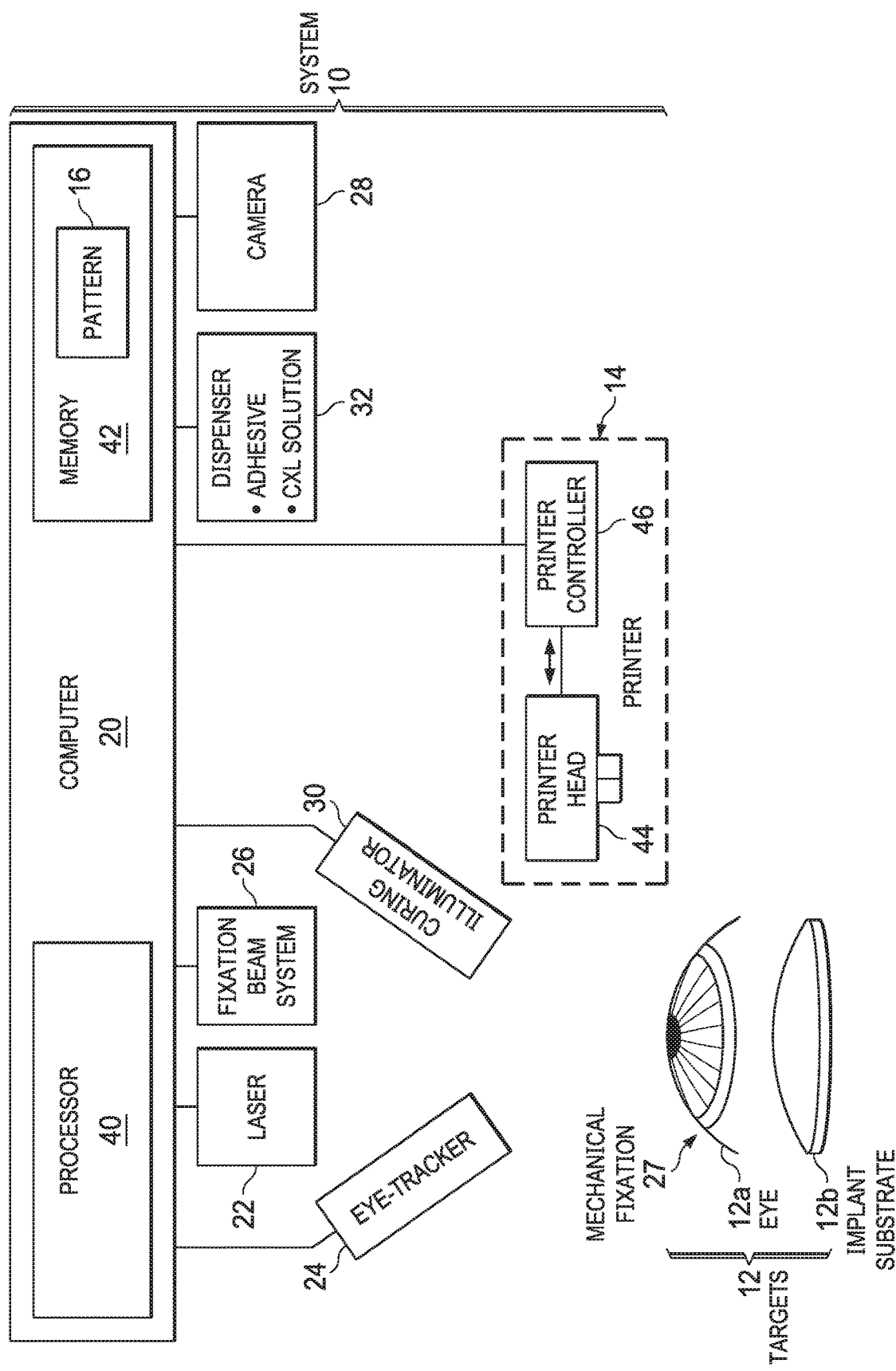
FIG. 1 illustrates an example of a system for refractive treatment of an eye.

FIG. 1 illustrates an example of a system 10 for refractive treatment of an eye 12a. System 10 includes a printer 14 that prints material (e.g., biological or biocompatible material) onto a print area of a target 12 according to a pattern 16 designed to provide refractive treatment for eye 12a. In some cases, target 12 may be eye 12a, and printer 14 prints the material directly onto eye 12a to perform the refractive treatment. In other cases, target 12 may be an implant substrate 12b. When implant substrate 12b is printed with the material, it yields an implant to be implanted into eye 12a for the refractive treatment.

In the illustrated embodiment, system 10 comprises a computer 20, printer 14, a laser 22, an eye-tracker 24, a fixation beam system 26, a mechanical fixation 27, a camera 28, a curing illuminator 30, and a dispenser 32. Computer 20 includes one or more processors 40 one or more memories 42 that stores pattern 16. Printer 14 includes a printer head 44 and a printer controller 46.

As an overview, in certain embodiments, computer 20 controls the components of system 10. Laser 22 prepares eye 12a for refractive treatment by, e.g., exposing an area of the cornea of eye 12a to be printed or making an incision within the cornea to receive an implant. Memory 42 stores pattern 16 designed to provide refractive treatment for eye 12a. Printer 14 prints material onto target 12 according to pattern 16. Fixation beam system 26 and/or mechanical fixation 27 stabilizes target 12 to reduce movement of target 12. Eye-tracker 24 tracks movement of target 12 and sends information describing the movement to computer 20, which in response can instruct printer 14 to compensate for the movement. Curing illuminator 30 illuminates the printed material with a light that promotes curing of the material. Dispenser 32 dispenses an adhesive that promotes adhesion of the material to target 12 and/or a cross-linking solution that promotes cross-linking within the cornea. Camera 28 generates images of the treatment to assist with monitoring the treatment.

System 10 provides refractive treatment for eye 12a. Refractive treatment involves a procedure that changes the refractive properties of eye 12a to improve vision. Pattern 16 indicates where material should be printed on a print area of target 12 in order to yield a result (e.g., a resulting corneal shape) that improves vision. For example, pattern 16 may indicate where material should be printed on a print area of eye 12a such that, after eye 12a recovers from the procedure, the printed material yields a shape for eye 12a that improves the vision of eye 12a. As another example, pattern 16 may indicate where material should be printed on a print area of an implant substrate 12b to yield an implant such that, after eye 12a recovers from the implantation procedure, the implant improves the vision of eye 12a. Examples of pattern 16 are illustrated in FIGS. 3 to 6.

In some embodiments, target 12 is an eye 12a, such as an eye of a human or other animal. In other embodiments, target 12 is an implant substrate 12b for an ocular implant. An ocular implant is an artificial aid surgically implanted into eye 12a to improve vision. Implant substrate 12b is a substrate onto which material may be printed to form an implant. Implant substrate 12b may comprise any suitable transparent biocompatible material, e.g., hyaluronan (also called hyaluronic acid) or collagen. Implant substrate 12b may have any suitable size or shape. For example implant substrate 12b may be circular or annular with a diameter in the range of 0.5 to 12 millimeters (mm), or in a sub-range such as 0.5 to 5 mm, 5 mm to 8 mm, and/or 8 to 12 mm. The print area of target 12 may be the area onto which material is printed.

To aid in description, this description uses a coordinate system commonly used in ophthalmological surgery. In this coordinate system, a laser beam operating on the eye defines the z-axis, and the xy-plane is the plane normal to the z-axis. Generally, the xy-plane coincides with the plane defined by the pupil, apex, or vertex of the eye.

Fixation beam system 26 and/or mechanical fixation 27 stabilizes target 12 to reduce movement of target 12. Fixation beam system 26 provides a fixation beam onto which the patient fixes their gaze to avoid moving eye 12a. Mechanical fixation 27 is affixed to eye 12a to reduce or prevent movement of eye 12a. Examples of mechanical fixation 27 include patient interfaces such as corneal suction rings.

Laser 22 prepares eye 12a for refractive treatment. Laser 22 may be any suitable laser surgical device that generates and emits a laser beam that interacts with (e.g., photodisrupt or photoablate) the cornea of eye 12a. A laser surgical device typically comprises laser source (e.g., femto or excimer) that generates a laser beam, and scanning components (e.g., optics) that direct the focus of the laser beam to specific points of the target. Laser 22 prepares eye 12a for treatment by interacting with the cornea in any suitable manner. For example, laser 22 may expose the print area of the cornea of eye 12a by creating a flap in the cornea or removing all or part of an epithelium of eye 12a (e.g. phototherapeutic keratectomy (PTK)). As another example, laser 22 may make an incision (e.g., a pocket) within the cornea to receive an implant. As another example, laser 22 may perform subsequent steps of the treatment. For instance, laser 22 may shape the cornea or printed material to yield prescribed refractive properties or perform other actions to complete the treatment. In certain embodiments, laser 22 may incorporate different laser sources that generate different laser beams, e.g., laser 22 may have sources that generate a beam that photodisrupts the corneal or printed material and a beam that ablates the corneal or printed material.

Printer 14 prints material onto the print area of target 12, and may comprise any suitable printer configured to deposit material onto a print area according to digital instructions. For example, printer 14 may be a 3D, or additive manufacturing, printer that deposits successive layers of material to yield the material configured in a specific shape and size. Printer 14 includes printer head 44 and printer controller 46. Printer head 44 directs material onto the print area and may be any suitable printer extruder that deposits material onto a surface. Printer controller 46 moves the printer head in the x, y, z directions to direct the material onto a specific location of the print area, and may receive instructions from computer 20 to move the printer head 44 according to pattern 16.

The material comprises any suitable transparent or semi-transparent material that is biological and/or biocompatible. Examples of such material include cultivated collagen material, human or animal cell material, biocompatible plastic, or hyaluronan. In certain cases, a material over which the epithelium can grow may be used. Such material may provide optimal nutrition of corneal cells and extra-cellular material, optical transparency over lifetime, and supportive surface properties for epithelium growth.

Eye-tracker 24 tracks movement of target 12 to aid in accurately printing the material on target 12. Eye-tracker 24 may track eye 12a, as a target eye 12a is more likely to move and need tracking than a target implant substrate 12b. However, eye-tracker 24 may be used to track any type of target 12. An eye-tracker detects translational and/or angular (or rotational) movement of eye 12a. In certain embodiments, image processing is used to locate the central point of eye 12a, e.g., the pupil, determine translational movement. Image processing is used to locate features of eye 12a (e.g., blood vessels, iris features, or any other appropriate feature) to determine angular movement.

When eye-tracker 24 detects movement of target 12, eye-tracker 24 notifies computer 20, which adjusts the instruction to printer controller 46 to compensate for the movement of target 12. For example, if target 12 is translates and/or rotates a certain amount, printer controller 46 compensates for the movement by translating and/or rotating pattern 16 that certain amount. In other embodiments, an interface may fix or hold target 12 in a desired location and position such that eye-tracker 24 may not be required. For example, a patient interface may hold eye 12a in place using, e.g., suction.

Curing illuminator 30 illuminates the print area with a light that cures the material. The light may cure the material by promoting cross-linking of the material and optionally the cornea of the eye. Examples of curing light include ultraviolet light or light (such as LED light) between 400 to 500 nm.

Dispenser 32 deposits a liquid onto target 12 during the procedure. For example, dispenser 32 directs onto eye 12a a corneal cross-linking solution that promotes cross-linking of the cornea of eye 12a. Examples of a corneal cross-linking solution include a riboflavin solution or other suitable solution. As another example, dispenser 32 directs onto the print area an adhesive that promotes adhesion of the material onto the print area. An adhesive may include fibrin.

Camera 28 generates an image of the print area to monitor the printing of the material. Camera 28 may comprise any suitable system that can generate an image of an object. Examples of camera 28 include an OCT system (such as a time domain or frequency domain OCT system) that generates OCT scans that can be used to create the image of the print area.

Figure 2:
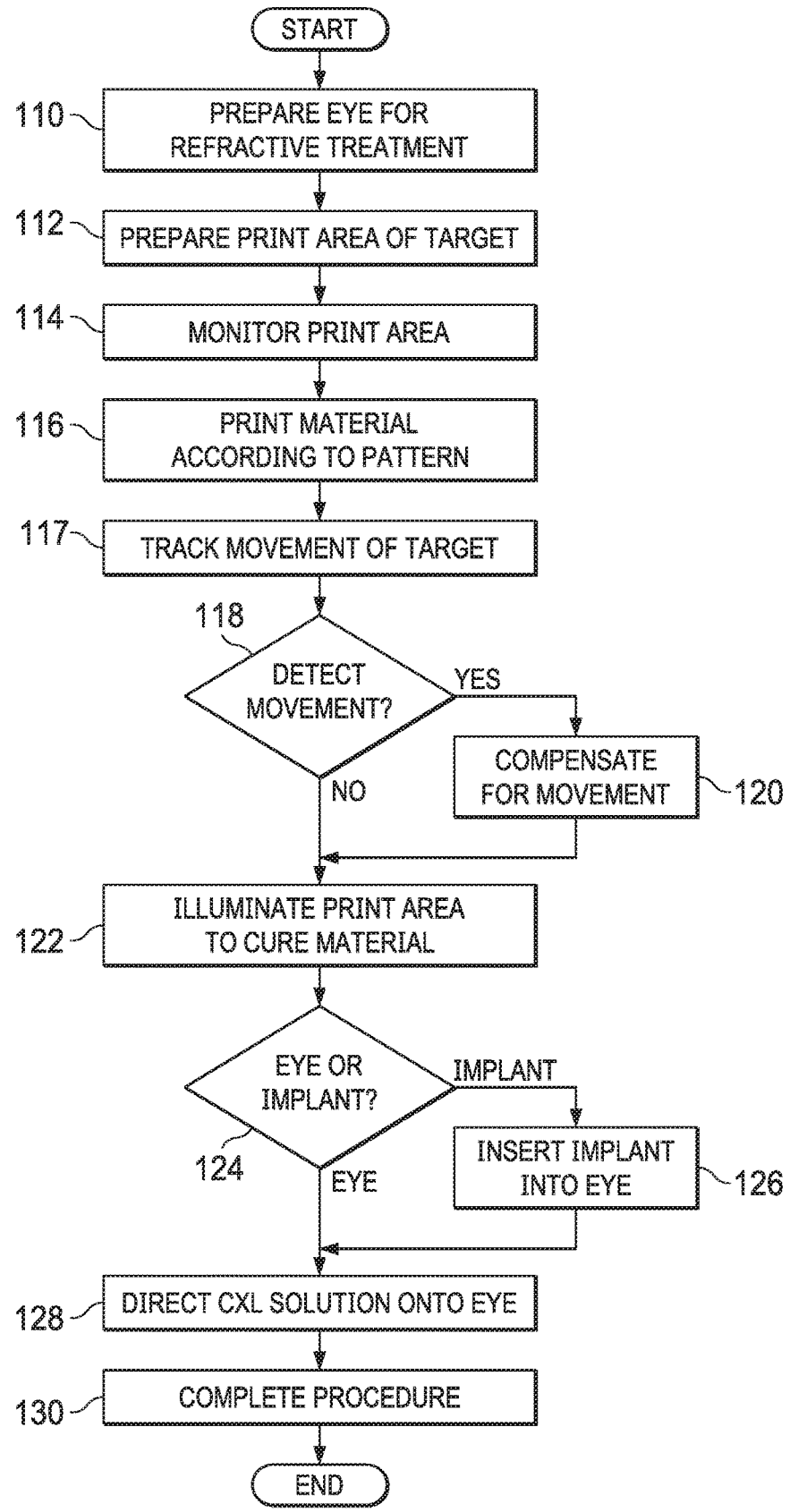
FIG. 2 illustrates an example of a method for refractive treatment of an eye.

FIG. 2 illustrates an example of a method for refractive treatment of an eye 12a by printing material on a target 12, which may be performed by system 10 of FIG. 1. The method starts at step 110, where laser 22 prepares eye 12a for refractive treatment. Depending on the procedure, laser 22 may: create a flap in the cornea of eye 12a to prepare for a LASIK procedure; create a pocket in the cornea designed to receive a corneal implant; or remove the epithelium of eye 12a to prepare for a PRK procedure.

Print area of target 12 is prepared at step 112. Target 12 may be eye 12a itself or an implant substrate 12b for an implant to be implanted into eye 12a. The print area may be prepared in any suitable manner. For example, dispenser 32 may direct an adhesive onto the print area that promotes adhesion of the material onto the print area. Camera 28 generates an image (such as a OCT scan image) of the print area at step 114 to monitor the printing of the material.

At step 116, printer 14 prints material onto the print area according to pattern 16 designed to provide refractive treatment for eye 12*a*. The material may be transparent material that is biological and/or biocompatible. Note, if target 12 is implant substrate 12*b*, step 116 may be performed prior to the procedure, such that step 116 occurs before step 110.

Eye-tracker 24 tracks movement of target 12 at step 117. Movement may be detected at step 118. If movement is detected, computer 20 receives information describing a movement of target 12 and instructs printer 14 to compensate for the movement. The method then moves to step 122. If no movement is detected, method moves directly to step 122. In embodiments that use a patient interface to fix target 12 into position, the method typically does not perform steps 117, 118, and 122.

Curing illuminator illuminates the print area at step 122 with a light that cures the material. Step 124 depends on the procedure and whether target 12 is eye 12*a* or implant substrate 12*b*. If target 12 is implant substrate 12*b*, the method moves to step 126, where the implant is inserted into eye 12*a*. The method then moves to step 128. If target 12 is eye 12*a*, the method moves directly to step 128.

At step 128, dispenser 32 directs a corneal cross-linking solution onto eye 12*a* that promotes cross-linking of the cornea. The procedure is completed at step 130, which depends on the procedure. For example, in a LASIK procedure, completing the procedure may involve closing the flap. The method then ends. After the method ends, the healing processes begin. For example, if the method removes the epithelium, it re-grows over the printed implant.

FIGS. 3 to 6 illustrate implants and deposited material that may be created using patterns 16 that guide the creation of the 3D shapes. A pattern 16 may be stored as a 3D printable file, such as the STL file format native to the stereolithography CAD software created by 3D Systems.

Figure 3:
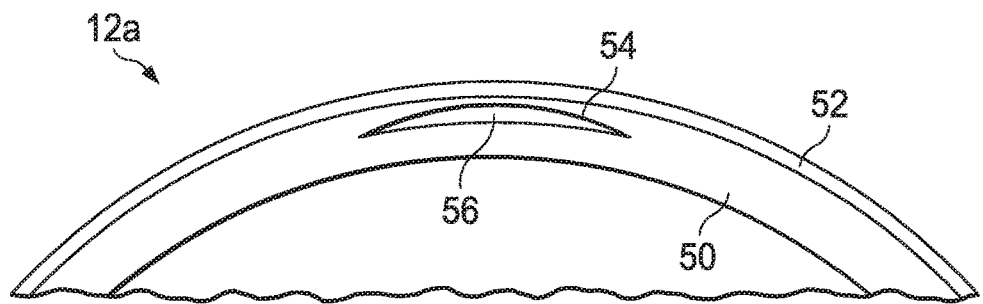
FIG. 3 illustrates an example of an implant created by the system of FIG. 1 for correction of hyperopia.

FIG. 3 illustrates an example of an implant 54 created by system 10 for correction of hyperopia. In the example, eye 12*a* has a cornea 50 and an epithelium 52. Implant 54 may have a shape similar to that of a contact lens, and is inserted into a pocket 56 of cornea 50.

Figure 4:
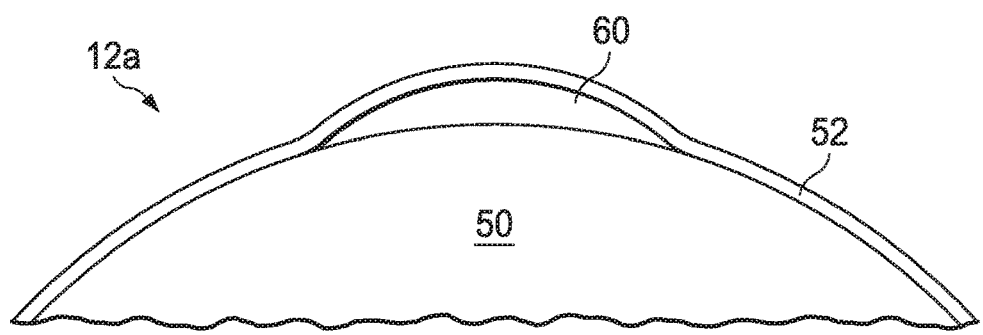
FIG. 4 illustrates an example of material deposited by the system of FIG. 1 for correction of hyperopia.

FIG. 4 illustrates an example of material 60 deposited by system 10 for correction of hyperopia. In the example, part of epithelium 52 is removed. System 10 deposits material 60 onto the exposed stroma of cornea 50 in a shape that corrects hyperopia. Deposited material 60 may have the shape of a thin layer disposed on the stroma. Epithelium 52 grows over material 60.

Figure 5:
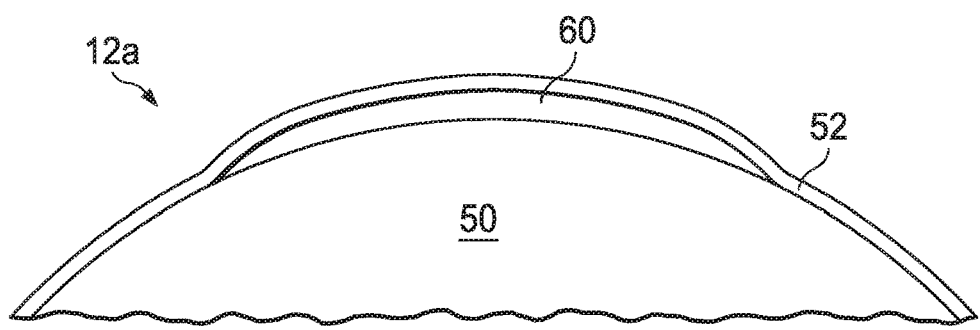
FIG. 5 illustrates an example of material deposited by the system of FIG. 1 for correction of astigmatism and/or improvement of biomechanical stability.

FIG. 5 illustrates an example of material 60 deposited by system 10 for correction of astigmatism and/or improvement of biomechanical stability (e.g., keratoconus). In the example, part of epithelium 52 is removed. System 10 deposits material 60 onto the exposed stroma of cornea 50 in a shape that corrects astigmatism and/or improves biomechanical stability. Deposited material 60 may have the shape of a dome disposed on the stroma. Epithelium 52 grows over material 60.

Figure 6:
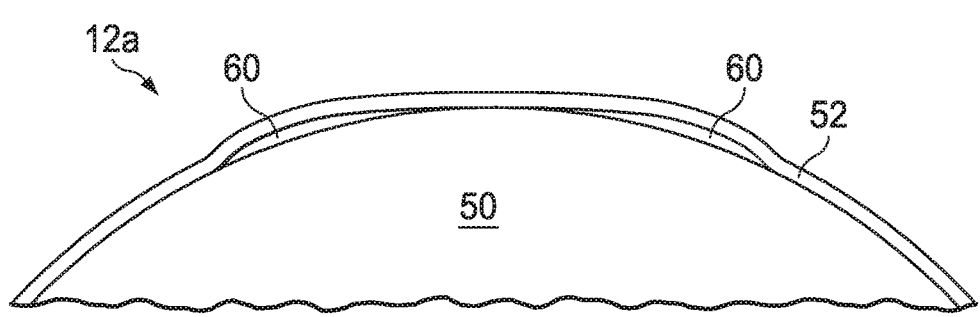
FIG. 6 illustrates an example of material deposited by the system of FIG. 1 for correction of myopia.

FIG. 6 illustrates an example of material 60 deposited by system 10 for correction of myopia. In the example, part of epithelium 52 is removed. System 10 deposits material 60 onto the exposed stroma of cornea 50 in a shape that corrects myopia. Deposited material 60 may have the shape of an annular ring disposed on the stroma. Epithelium 52 grows over material 60.

A component (e.g., a computer) of the systems and apparatuses disclosed herein may include an interface, logic, and/or memory, any of which may include hardware and/or software. An interface can receive input to the component, provide output from the component, and/or process the input and/or output. Logic can perform the operations of the component, e.g., execute instructions to generate output from input. Logic may be a processor, such as one or more computers or one or more microprocessors. Logic may be computer-executable instructions encoded in memory that can be executed by a computer, such as a computer program or software. A memory can store information and may comprise one or more tangible, non-transitory, computer-readable, computer-executable storage media. Examples of memory include computer memory (e.g., Random Access Memory (RAM) or Read Only Memory (ROM)), mass storage media (e.g., a hard disk), removable storage media (e.g., a Compact Disk (CD) or a Digital Video Disk (DVD)), and network storage (e.g., a server or database).

Although this disclosure has been described in terms of certain embodiments, modifications (such as substitutions, additions, alterations, or omissions) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

What is claimed is:

1. A system for performing refractive treatment of an eye, comprising:
   a laser configured to emit a laser beam to prepare the eye for the refractive treatment;
   a printer configured to print material onto a print area of a target, the printer comprising:
      a printer head configured to direct the material onto the print area; and
      a printer controller configured to move the printer head to direct the material onto a specific location of the print area;
   a computer comprising:
      a memory configured to store instructions for a pattern for the target, the pattern designed to provide the refractive treatment for the eye; and
      one or more processors configured to:
         instruct the printer controller to move the printer head to print the material onto the print area according to the pattern; wherein the target is an eye and the print area is a located in a cornea of the eye; and further wherein the material is printed onto a stroma of the cornea in a shape that corrects hyperopia.

2. The system of claim 1:
   further comprising an eye-tracker configured to track movement of the target;
   the one or more processors further configured to:
      receive information describing a movement of the target; and
      adjust the instruction to the printer controller to compensate for the movement of the target.

3. The system of claim 1, further comprising an interface configured to hold the target at a specific location and position.

4. The system of claim 1, the target comprising an implant substrate for an implant configured to be implanted into the eye.

5. The system of claim 1, the laser configured to prepare the eye by creating a flap in the cornea of the eye.

6. The system of claim 1, the laser configured to prepare the eye by creating a pocket in the cornea of the eye.

7. The system of claim 1, the laser configured to prepare the eye by removing an epithelium of the eye.

8. The system of claim 1, further comprising a curing illuminator configured to illuminate the print area with a light that cures the material.

9. The system of claim 1, further comprising a dispenser configured to direct a corneal cross-linking solution onto the eye that promotes cross-linking of the cornea of the eye.

10. The system of claim 1, further comprising a dispenser configured to direct an adhesive onto the print area that promotes adhesion of the material onto the print area.

11. The system of claim 1, further comprising a camera configured to generate an image of the print area to monitor the printing of the material.

12. The system of claim 1, the material comprising a biological or biocompatible material.

13. The system of claim 1, the laser further configured to perform a subsequent step of the refractive treatment.

14. A method for performing refractive treatment of an eye, comprising:
   emitting, from a laser, a laser beam to prepare the eye for the refractive treatment;
   communicating, by a computer, with a printer configured to print material onto a print area of a target, the printer comprising a printer head and a printer controller, the printer head configured to direct the material onto the print area, the printer controller configured to move the printer head to direct the material onto a specific location of the print area; and
   accessing, by the computer, instructions for a pattern for the target, the pattern designed to provide the refractive treatment for the eye; and
   instructing, by the computer, the printer controller to move the printer head to print material onto the print area according to the pattern; wherein the print area is a located in a cornea of the eye; and further wherein the material is printed onto a stroma of the cornea in a shape that corrects hyperopia.

15. The method of claim 14, further comprising:
   tracking, using an eye-tracker, movement of the target;
   receiving information describing a movement of the target; and
   adjusting the instruction to the printer controller to compensate for the movement of the target.

16. The method of claim 14, further comprising:
   providing an interface configured to hold the target at a specific location and position.

17. The method of claim 14, further comprising:
   illuminating the print area with a light that cures the material.

18. The method of claim 14, further comprising:
   directing a corneal cross-linking solution onto the eye that promotes cross-linking of the cornea of the eye.

19. The method of claim 14, further comprising:
   directing an adhesive onto the print area that promotes adhesion of the material onto the print area.

* * * * *